(12) United States Patent
Harwood

(10) Patent No.: US 6,685,474 B2
(45) Date of Patent: Feb. 3, 2004

(54) AQUEOUS SLURRIES USEFUL FOR CLEANING TEETH AND METHODS RELATED THERETO

(76) Inventor: Douglas B. Harwood, 5614 Cape George Rd., Port Townsend, WA (US) 98368

( * ) Notice: Subject to any disclaimer, the term of this patent is extended or adjusted under 35 U.S.C. 154(b) by 0 days.

(21) Appl. No.: 10/223,060

(22) Filed: Aug. 15, 2002

(65) Prior Publication Data

US 2003/0026769 A1 Feb. 6, 2003

Related U.S. Application Data

(63) Continuation-in-part of application No. 09/773,081, filed on Feb. 1, 2001, now abandoned.

(51) Int. Cl.[7] .................. A61K 7/16; A61K 33/44; A61C 5/00
(52) U.S. Cl. ............ 433/217.1; 424/49; 424/125
(58) Field of Search ............... 424/49–58, 125; 433/217.1

(56) References Cited

U.S. PATENT DOCUMENTS

| | | | | |
|---|---|---|---|---|
| 3,954,115 A | | 5/1976 | Bengtsson | 132/89 |
| 4,270,556 A | | 6/1981 | McAllister | 132/89 |
| 4,271,854 A | | 6/1981 | Bengtsson | 132/89 |
| 4,434,235 A | * | 2/1984 | Rabi et al. | 436/110 |
| 4,477,259 A | * | 10/1984 | Funk | 44/280 |
| 4,501,205 A | * | 2/1985 | Funk | 44/280 |
| 4,878,508 A | | 11/1989 | Durbin | 132/329 |
| 5,162,202 A | * | 11/1992 | Shamsuddin | 435/25 |
| 5,302,287 A | * | 4/1994 | Losack | 134/42 |
| 5,368,411 A | * | 11/1994 | Losack | 134/40 |
| 5,393,229 A | | 2/1995 | Ram | 433/118 |
| 5,419,209 A | * | 5/1995 | Sepe | 73/863 |
| 5,681,564 A | * | 10/1997 | Saulson | 424/126 |
| 5,711,935 A | | 1/1998 | Hill et al. | 424/49 |
| 5,875,798 A | | 3/1999 | Petrus | 132/321 |
| 6,001,258 A | * | 12/1999 | Sluys et al. | 210/650 |
| 6,328,028 B1 | * | 12/2001 | Cayse et al. | 44/519 |

FOREIGN PATENT DOCUMENTS

| | | |
|---|---|---|
| DE | 26 37 862 | 3/1978 |
| JP | 2000-128751 | 5/2000 |

* cited by examiner

Primary Examiner—Shep K. Rose
(74) Attorney, Agent, or Firm—Seed IP Law Group PLLC

(57) ABSTRACT

Novel aqueous slurries capable of removing calculus, plaque or stains, adherent to tooth surfaces of a warm-blooded animal, when used in methods that are self-practicable by an individual human or practicable by an individual human on another warm-blooded animal, combine finely-divided charcoal; water; and alcohol, ammonia or hydrogen peroxide to form the slurries. Also disclosed are self-practicable methods that utilize the disclosed aqueous slurries by applying to, and contacting affected tooth surfaces with, the same, then removing the treated calculus, plaque or stains by means of devices and techniques that are safe to use according to the methods. Further, kits are disclosed that comprise the disclosed aqueous slurries, as well as apparatus, devices and tools for effectively using the same for the above purposes.

4 Claims, No Drawings

AQUEOUS SLURRIES USEFUL FOR CLEANING TEETH AND METHODS RELATED THERETO

BACKGROUND OF THE INVENTION

1. Field of the Invention

The present invention generally relates to compositions and methods useful for oral hygiene, and more particularly to such compositions and methods that are self-practicable by a human, or that can be practiced by a human on another human or other warm-blooded animal, for indicating the presence of and removing both plaque and calculus, as well as removing stains, adherent to tooth surfaces of the human or other warm-blooded animal.

2. Description of the Related Art

Practicing good oral hygiene is critical in the prevention of tooth decay and periodontal, or gum, disease. Periodontal disease is one of the most prevalent chronic diseases affecting humans and other mammals. Children as young as 5 years of age can have the disease. By the age of 35, three out of four people are affected, and by age 65, an estimated 98 percent of Americans have periodontal disease.

Before the onset of disease, healthy pink gingiva, or gum tissue, surrounds the teeth. Gum tissue, which is the soft tissue covering the neck of the tooth, serves to hold teeth in place and prevent infectious material from entering the jaw bone or tooth itself. The area between the tooth enamel and the gigiva is called the gingival crevice. Gums are constantly exposed to bacteria. Gingivitis typically develops when large masses of bacteria fill the gingival crevice, and is first manifested by bleeding gums. This inflammatory condition is reversible. Gum disease occurs when the gingival crevice between the tooth and gum is more than 3 mm deep.

As gingivitis progresses, the tissue surrounding the teeth is destroyed and the supporting collagen fibers degenerate, leaving abnormally deep (1 to 3 mm) crevices, or pockets adjacent to the teeth due to the loss of gum attachment thereto. As the pockets grow, and the amount of bacteria therewithin increases, the gums recede down the root of the teeth. Eventually, the bone supporting each affected tooth socket degenerates and results in tooth loss. These are the defining characteristics of periodontal disease. In fact, the latter is the principal reason that adults have teeth removed. Typically, this is a slow, painless, progressive disease and, hence, is insidious in nature.

More specifically, periodontal disease is caused by certain types of bacteria that form a clear (almost invisible), sticky, film of the bacteria, having an organized structure and referred to as dental plaque (hereinafter, "plaque"). Plaque is not food or food residue. Plaque forms at all ages and on both non-permanent ("baby") and permanent (adult) teeth. It adheres to the surfaces of teeth, gum tissues, dental restorations, and even the tongue and is adherent to the point that it cannot be washed or rinsed off. Instead, plaque must be removed mechanically. Brushing and flossing are most commonly used. Picking and scraping may also be used. Such techniques are effective in removing the plaque that is, in fact, accessed thereby.

Studies have shown that plaque forms very soon after it is removed—from as soon as five minutes, to up to four hours after removal. It is fair to say that plaque must be continually removed and that its formation cannot be stopped. When all oral hygiene measures are suspended, gingivitis can result from the presence of plaque within about three weeks. As noted, gingivitis is reversible. With diligent flossing and toothbrushing, the inflammatory condition usually disappears. In the absence of such measures, periodontal disease is sure to follow. Plaque also causes tooth decay (cavities).

Despite normal diligence in removal of plaque, which may be regarded as thoroughly brushing teeth twice a day, and proper flossing between all teeth daily, some amount of plaque remains. Thus, the formation of calculus (also referred to as tartar), which stems from the presence of plaque, appears to be inevitable. In fact, research has shown that about 92% of Americans have a significant accumulation of calculus in their mouths. Calculus forms when the calcium carbonate and phosphate in saliva combine with plaque at the tooth surface and precipitates to form a hard and tough, unsightly scale deposit not unlike a limestone type substance. Once the deposit mineralizes, it can grow rather quickly. Typically, calculus is yellow or brown in color. It bonds cohesively with teeth and, unlike plaque, cannot be removed by normal brushing or flossing.

Calculus can exist both above the gum line as a hard deposit on the top portion of teeth (supragingival calculus), and below the upper gum surface (subgingival calculus). Supragingival and subgingival calculus deposits are equally hard and adherent. The surface of calculus tends to be rough and filled with microscopic holes. In fact, when examined under a microscope, it is apparent that calculus has a myriad of nooks and crannies, not unlike a coral reef.

The removal of calculus is an important aspect of good dental hygiene for a number of reasons. First, as noted above, it is unsightly due to its yellow or brown color. Also, it absorbs stains easily. Therefore, its removal is important from an aesthetic standpoint. Second, the microscopic holes found therein harbor food particles, bacteria, and viruses that cause swelling and bleeding of the gums. Third, the rough surface of calculus both attracts bacterial plaque to tooth surfaces, and enhances its adherence thereto, making thorough plaque removal more difficult. When this layer of plaque mineralizes, more calculus forms, and the result is a continuous cycle of accumulation. This cycle is particularly problematic in the case of subgingival calculus and is a significant contributor to more extreme conditions of gingivitis and periodontal disease. In the case of supragingival calculus, this cycle is also problematic, principally as a contributor to tooth decay.

As noted, hard calculus cannot be removed by normal brushing and flossing. Typically, it is mechanically removed by dentists and dental hygienists by scraping, picking, drilling and abrading with metal instruments having hard, sharp edges and tips. Often, the movement of the instruments is by manual manipulation, although, for example, an oscillating device, typically having a metal tip and operating at ultrasonic frequencies, may be used. Such removal of calculus is most often performed on a patient on a rather infrequent basis. Twice a year is usually recommended. Often, patients will avail themselves of such calculus removal only once a year, or less frequently.

One of the principal disadvantages of this approach to calculus removal is associated with the infrequency of the removal. The extended period of time between visits to the dentist is likely to allow significant accumulation of calculus and plaque, and, thus, the tooth decay and gingivitis that is often associated therewith. A resultant, additional disadvantage is the pain and discomfort associated with the calculus removal (especially when gingivitis is extant) and the repair of damage often caused by the accumulation of calculus and plaque (e.g., drilling to remove decayed tooth matter and filling the tooth to replace the same. Other resultant disadvantages include the considerable expense and inconvenience associated with the above.

If the individual patient could self-practice the above techniques, used by dentists and dental hygienists, for calculus removal, as part of a frequent and regular, personal oral hygiene regimen, some of the above disadvantages could be avoided. However, such use of the methods and instruments, typically used by the skilled dental practitioner on a patient, would be hazardous and likely to result in serious injury to teeth, gingiva, and other soft tissues in the mouth. Accordingly, various methods, devices and compositions, other than those associated with conventional tooth brushing and flossing, have been described as allegedly suitable for use by a patient to remove at least some calculus as part of personal oral hygiene, while avoiding the risk of such injury.

For example, U.S. Pat. No. 4,878,508 describes a device that can be used for personal oral hygiene for removal of plaque and tartar. The device is essentially an arcuate pick having a pointed lead end and a more wide, truncated end. The pick is made of a resilient material, has two sides that are joined to form a V-shaped cross-section, and includes cilia, spaced ridges, and bristles along the sides. Also, the edges of the two sides are beaded to avoid cutting gingival tissue. U.S. Pat. No. 5,711,935 describes bundled, multi-fiber dental floss that is loaded with agents, including abrasives and anti-tartar agents, and that presumably could have some utility in removal of calculus.

A hand-held device having an oscillating (at a frequency of at least 5 Khz) head with a wooden toothpick releasably attached thereto, is described by U.S. Pat. No. 5,393,229. The device is described as suitable for use by dental professionals to clean a patient's teeth, or by an individual for personal use, by virtue of using a wooden toothpick, rather than a metal tip. The device is further described as able to hold a toothpick in either a perpendicular or coaxial orientation with respect to its head for cleaning between teeth and between teeth and gingiva. Also disclosed, is coating the toothpick with various reagents, including an anti-calculus agent such as citric acid or pyrophosphate. However, there is no assertion made therein that the device provides an effective means for calculus removal.

U.S. Pat. No. 4,270,556 describes a device allegedly useful for removal of plaque, calculus and stains from interproximal tooth surfaces without abrading or damaging tooth enamel. The device is essentially a very thin stainless steel strap that is perforated, the perforations having raised peripheral edges useful for scaling or scraping. Also, the stainless steel used is disclosed as softer than tooth enamel so as not to damage the same. The device is used in much the same manner as dental floss.

U.S. Pat. No. 5,875,798 mentions that toothpicks have a number of utilities, including: removing food particles, stimulating gum tissue, and removing both plaque and calculus. Also mentioned is the existence of dental floss that contains, among other agents, anti-tartar agents such as tetrasodium pyrophosphate, sodium acid pyrophosphate and tetra potassium pyrophosphate. Disclosed as novel therein is a toothpick that includes a saliva-soluble coating near an end thereof, where the coating comprises anti-tartar agents.

A toothpick, described as novel and allegedly capable of removing calculus, is also disclosed in U.S. Pat. No. 3,954,115. The disclosed toothpick is resilient, being made from a synthetic resin, and includes a chisel-shaped end and roughened or knurled sides, adapted for scraping and abrading tooth surfaces, respectively, when the toothpick contacts the same in a reciprocating fashion. U.S. Pat. No. 4,271,854 describes a pliable toothpick, made from injection moldable material, and having a rigid middle portion and tapered, arcuate end portions. At least some of the end portion surface is roughened and, thereby, abrasive. The toothpick is described as capable of removing early stages of tartar scale from interproximal and proximal tooth surfaces by means of contacting the same with the roughened surface of an end portion in a reciprocating fashion.

Also described, in addition to the above-discussed devices and related methods, as allegedly suitable and effective for removing at least some calculus as part of a personal oral hygiene regimen, are various compositions that can be used with otherwise conventional brushing methods. For example, German Patent No. DE 2637862 describes a powdered tooth care composition comprising 10–95% charcoal, 5–25% walnut bark, and 1–15% NaCl that is allegedly capable of removing both plaque and calculus. Also, Japanese Patent No. 2000128751 describes a toothpaste that is 0.05 to 5%, by weight, hard charcoal powder and that is to be applied by ordinary tooth brushing. Assertedly, the described toothpaste allows for the removal of already deposited dental calculus.

As the above-described devices and compositions, and methods related thereto, have limited effectivity with regard to the removal of both subgingival and supragingival calculus and/or present excessive risk of injury to teeth, gingiva or other soft tissues in the mouth when self-practiced, there remains a need in the art for devices and/or compositions, and methods related thereto, that can, when self-practiced, be used safely, easily and effectively to remove calculus from teeth, in addition to plaque and stains. The benefit of such devices and/or compositions, and methods related thereto, with regard to calculus removal should at least suffice to effectively supplement the benefit of less frequent calculus removal performed by dental professionals. The present invention fulfills these needs and provides further related advantages.

BRIEF SUMMARY OF THE INVENTION

In brief, the present invention is directed to aqueous slurries useful for removing both plaque and calculus, as well as stains, from affected tooth surfaces when applied directly thereto so as to contact the calculus, plaque or stains to be removed, and combined with mechanical removal of the same. The present invention, in another aspect, is also directed to methods, self-practicable by individual humans ("individuals" or "patients") in need thereof or practicable by individuals on patients or other warm-blooded animals, for removing both plaque and calculus, as well as stains, from tooth surfaces that use the above slurries in combination with mechanical application of the same, as well as mechanical removal of the calculus and/or plaque and/or stains contacted with the slurries.

In yet another aspect, the present invention is directed to kits, useful for such removal, that include the above slurries or the components (i.e., charcoal and liquid portion) thereof, as well as a means for measuring and mixing the components, a means for effectively applying the slurries to affected tooth surfaces, and a means for removing the treated calculus, plaque or stains.

More specifically, in one embodiment, the present invention is directed to slurries, useful for removing calculus, plaque or stains adherent or otherwise attached to tooth surfaces, wherein the slurries are formed by combining finely-divided charcoal and a liquid portion so as to create a slurry therefrom, the liquid portion comprising water, as well as alcohol, ammonia or hydrogen peroxide. Such slurries have been found to be surprisingly effective in removing both plaque and calculus adherent to tooth surfaces, even when self-administered by an individual in need thereof.

In another embodiment, the present invention is directed to a method for removing calculus, plaque or stains adherent to tooth surfaces, the method being self-practicable by an individual in need thereof or practicable by an individual on another individual or another warm-blooded animal and using the above slurries. The method, as applied, for example, to the removal of calculus, comprises: coating affected tooth surfaces with an effective amount of any of the above slurries; then contacting, for an effective period of time, the calculus to be removed and now having the aqueous slurry coated thereupon; optionally, repeating the above steps as necessary or desired; then, mechanically removing the contacted calculus from the affected tooth surfaces; optionally, repeating the above steps until a desired extent of removal of the calculus from the affected tooth surfaces and oral cavity is accomplished; and, finally, mechanically and/or rinsingly removing any residual slurry and loosened calculus from the affected tooth surfaces and other tooth surfaces, as well as from other surfaces of the oral cavity. Basically, the same method can be used to remove plaque from affected tooth surfaces.

The coating step (i.e., first step), optionally combined with the contacting step (i.e., second step) of the above method, also provides a method for visually indicating the presence of calculus or plaque adherent to tooth surfaces. The method for such indicating is another aspect of the present invention.

In yet another embodiment, disclosed is a kit adapted for removing calculus, plaque or stains adherent to tooth surfaces in the oral cavity of an individual in need thereof. The kit is intended for use by the individual, with or without the assistance of another. The kit includes a quantity of any of the above aqueous slurries, or quantities of components thereof, namely, a quantity of finely-divided charcoal and quantities of the constituents of a liquid portion or a quantity of the liquid portion. The kit further includes, where the kit contains the components of the aqueous slurry to be used, a container and device adapted to mix quantities of the components in a desired ratio; an applicator for coating affected tooth surfaces with the slurry; a device adapted to cause, by mechanical action, the applied slurry to agitatively and frictionally contact the tooth surfaces and adherent plaque and calculus coated thereby and, further, to coat and contact, as described above, tooth surfaces not coated with the slurry by means of the applicator; a device adapted to mechanically remove the plaque and calculus, thus contacted, from the affected tooth surfaces; and, optionally, a device and/or rinsing agent adapted to mechanically or rinsingly remove any residual portion of the slurry, as well as any loosened plaque or calculus not already removed, from the affected tooth surfaces and other tooth surfaces, as well as the other surfaces of the oral cavity.

These and other aspects of the present invention will be evident upon reference to the following detailed description of the invention.

DETAILED DESCRIPTION OF THE INVENTION

As mentioned above, the present invention is directed to aqueous slurries useful, when applied by an individual human (hereinafter, "individual" or "patient") for personal oral hygiene or when applied to another warm-blooded animal, including an individual (hereinafter, "subject"), for indicating the presence of, and removing, both plaque and calculus, particularly calculus, as well as for removing stains, from affected tooth surfaces, and to related methods and kits. The terms "teeth" and "tooth," as used herein, refer to the teeth of warm-blooded animals, including a human. The expressions "calculus or plaque," as used herein, means calculus and/or plaque. Further, the expression "calculus, plaque or stains," as used herein, means calculus and/or plaque and/or stains.

In one embodiment, disclosed is such an aqueous slurry formed by combining and mixing finely-divided charcoal and a liquid portion, where the liquid portion, in related embodiments, comprises water combined with alcohol, ammonia or hydrogen peroxide. As used herein, the expression "finely-divided charcoal" also refers to powdered charcoal, finely-divided or powdered carbon, or activated charcoal—all of which are hereinafter referred to by the term "charcoal." As is known to those skilled in the art, charcoal is typically black in color and derived from carbonaceous materials such as wood, peat and coconut shells to yield an odorless, tasteless form of carbon that is safe for consumption by humans and other mammals. Uses include neutralizing drugs and poisons; providing intestinal gas relief; preventing intestinal infections; purifying air, water, foodstuffs, chemicals and pharmaceuticals; and cleaning surfaces, including tooth surfaces.

Charcoal products are readily commercially available. Some examples of products that are particularly suitable for the present invention are the charcoal products manufactured and sold by Norit Americas Inc. (Atlanta, Ga.) and designated as Norit®A Supra, Norit®B Supra, and Norit®E Supra. The laster products comprise carbon particles, 97% (by weight) of which are less than 150 microns in diameter. Various sizes of carbon particles can be used. Generally desirable, are particle sizes that allow the carbon particles to become suspended in the liquid used for the composition, and that allow the carbon particles to be mechanically or fluidly transported to and away from interproximal tooth surfaces and tooth surfaces in the gingival crevice, in addition to proximal tooth surfaces.

In a particular related embodiment, the liquid portion comprises water and alcohol as miscible mixture thereof. Such mixtures, such as rubbing alcohol, are either readily commercially available, or readily prepared from water and various alcohols. A few examples of alcohols that can be used are methanol, ethanol and propanol (including isopropyl alcohol. Various concentrations of alcohol in water are suitable. In a related embodiment, the concentration of the alcohol in the water ranges from about 25% to about 70%, by volume.

In a further, more particular related embodiment, the alcohol is provided by ordinary, commercially available mouthwash, such as Listerine® (Warner-Lambert Consumer Healthcare, Morris Plains, N.J.), Scopeo® (Proctor& Gamble, Cincinnati, Ohio) and Plax® (Pfizer, Inc., New York, N.Y.), to name a few. As used herein, the term "mouthwash" is synonomous with the term "mouthrinse." The mouthwash is simply combined and mixed with a quantity of charcoal to form a slurry. Various relative amounts of mouthwash and charcoal may be used. Also, the mouthwash may be used in preparing the slurry when in a concentrated form, as purchased off the shelf, or after being diluted with water.

As noted, disclosed in one embodiment is an aqueous slurry formed by slurrying charcoal in a liquid portion that comprises water and ammonia. More particularly, the liquid portion is a solution of ammonia in water. Such solutions are readily commercially available and prepared by methods well known to those skilled in the art.

Also as noted, in another embodiment of the present invention, disclosed is an aqueous slurry comprising charcoal slurried in a liquid portion that comprises water and hydrogen peroxide. Aqueous solutions of hydrogen peroxide are prepared by methods well known in the art and are used for bleaching, oxidizing, deodorizing, and disinfecting. When the concentration of the hydrogen peroxide in the aqueous solution is at least about 3% by weight, the solution is used medicinally as a disinfectant, for example, to cleanse wounds. Such solutions are readily commercially available.

It has been surprisingly and unexpectedly found that, when the disclosed slurries are used as described below, they are effective to indicate the presence of plaque and calculus and to remove the same from tooth surfaces to an extent greater than that achievable with charcoal alone (i.e., charcoal and saliva) or with charcoal and water when used in a similar fashion. While not wishing to be bound by any theory, Applicant believes that the above finding stems from the ability of the aqueous slurries disclosed herein to at least partially dissolve and, thus, soften, calculus when applied thereto and intimately contacted therewith, as described below.

Again, not wishing to be bound by any theory, it is also believed that such dissolution and softening allows the black charcoal in the disclosed slurries to mix with and adhere to the calculus, thus, accounting for the ability of the slurries to serve as an indicator of the presence of calculus adhering to tooth surfaces. Such indication of its presence, as well as the at least partial dissolution and softening thereof by the slurries, expedite the removal of adherent calculus by the methods discussed below, such methods heretofore having been effective only in removing plaque.

Other surprising and unexpected advantages are associated with the use of the disclosed aqueous slurries. Specifically, the disclosed slurries provide the unexpected results described above, while further providing the unexpected benefits of less irritation during use to gingival tissue, generally less pain during use, and less abrasion of tooth enamel, as compared to using charcoal only, charcoal and water, or other methods. More particularly, the disclosed slurry that comprises charcoal slurried in water and ammonia surprisingly exhibits nerve-deadening properties. Another benefit of the disclosed slurries is their allowing for the removal of calculus, plaque and stains from tooth surfaces in a more antiseptic environment.

In another aspect, the present invention is directed to a method for removing calculus, plaque and stains from the teeth of an individual or subject, where the method is self-practicable by an individual or practicable by an individual on a subject. The first step of the method is applying an effective quantity of a disclosed aqueous slurry to affected tooth surfaces so as to coat the calculus, plaque or stain adherent thereto. As would be appreciated by one skilled in the art, any one of a variety of means for so applying the slurry may be used. In one related embodiment, tooth and gingival surfaces, and other surfaces in the oral cavity, are so coated by taking an effective quantity of the slurry into the oral cavity and swishing the slurry therearound so as to coat the various surfaces therein.

In another related embodiment, an application means is used to apply disclosed aqueous slurries to affected tooth surfaces. Various application means can be used and include, as some examples, fingertips, floss, a toothbrush, a cotton-tipped toothpick, or a cotton swab. A toothbrush and a cotton swab are, for example, particularly suitable for applying the compositions to proximal tooth surfaces, while a cotton-tipped pick and floss are, for example, more suitable for applying the slurries to affected tooth surfaces that are interproximal or subgingival. The picks and swabs need not be tipped with cotton. Any absorbent material capable of efficiently transporting the disclosed slurries to affected tooth surfaces without damaging the latter, or other surfaces in the oral cavity, may be used.

The second step of the disclosed method is contacting, for an effective period of time, the affected tooth surface with the aqueous slurry applied thereto. In a related embodiment, the contacting step comprises agitative and frictional contact between the affected tooth surface and the slurry applied thereto. Generally, to accomplish such contact, the surface of a device is directly rubbed against or upon the calculus, plaque or stains adherent to the affected tooth surface while a quantity of the slurry is resident between the device and tooth surfaces. Surprisingly, effective removal of calculus, plaque and stains is accomplished even with gently rubbing.

Devices should be used that can be rubbed against the tooth and gingival surfaces without causing damage or injury thereto. Brushes and swabs tipped with cotton or another soft, absorbent material are particularly suitable for this purpose. Also, they can be used to hold and apply additional quantities of the slurries during the rubbing step. Fingertips may also be used.

For interproximal and subgingival areas of tooth surface, floss can be used, as can any of various types of picks such as those described previously. For example, resilient picks made from wood, including bamboo, or resinous material may be used. The picks may or may not have a roughened surface or a surface comprising raised portions adapted for scraping or abrading. Picks that taper, at least on one end, to a fine point, are particularly useful for interproximal and subgingival areas. Different motions can effect the agitative and frictional contact between the device and tooth surface, and may be characterized as a back and forth, or reciprocating motion, a circular motion, or a scraping motion.

The aqueous slurry may be so applied to and contacted with affected tooth surfaces, optionally, in a repeated alternating fashion for an effective period of time. Such a period of time would at least be of sufficient duration to allow for the indication by staining, as well as the at least partial dissolution, or softening, of calculus adherent to tooth surfaces. This is manifested by the appearance of a black material having a surface characterized by a viscous, sticky appearance. Typically, the material comprises plaque and at least a portion of the calculus that has been softened to the point that it can be mechanically removed by methods described below.

The aforementioned removal is the third step of the disclosed method and is accomplished using essentially the same devices used with the aqueous slurries to create the softened calculus. Accordingly, the material is removed from tooth surfaces and from the oral cavity, for example, on the surface of floss, a brush, a swab or a pick, having been transferred to the surface by scraping, brushing, or rubbing the device or devices against the tooth surface having the material thereon. Then, either the material is transferred from the device for disposal and the device reused, or the device with material thereon is discarded and a new, clean device is then used for additional material removal. Also, additional slurry, or liquid, used for the preparation thereof, or charcoal can be applied to the device to expedite removal of the softened calculus and/or plaque. Some other liquid cleaner or toothpaste could also be used. A vacuum device could also be used for material removal, alone or in combination with the above-described devices.

Characteristically, calculus deposits are removed, as described above in a gradual, layer-by-layer fashion. Accordingly, the above steps are typically repeated until all or a desired degree of the calculus, plaque or stain is removed.

The final step of the disclosed method is removing residual amounts of slurry remaining in the oral cavity, as well as any loose portions comprising calculus or plaque. As one example, this may be accomplished by conventional brushing of tooth and other surfaces in the oral cavity with toothpaste, followed by rinsing with water.

It may be appreciated that the aqueous slurries used for the above-disclosed method may be prepared by combining and mixing the charcoal and liquid portion prior to applying the slurry to the affected tooth surfaces, or may be combined and mixed in situ, that is, in the oral cavity. For example, in the latter case, the liquid portion is first applied to tooth surfaces by introducing a bulk quantity thereof into the oral cavity and swishing it about therein and thereafter expelling any excess amount, or by using an applicator as described above. Then, the charcoal can be applied to the tooth surfaces using, for example, the same devices and methods described above for rubbing the surfaces with the slurry. The charcoal and liquid portion are then mixed to yield the slurry during the course of rubbing the tooth surfaces.

In another aspect, the present invention is directed to a method for indicating the presence of calculus or plaque adherent or attached to tooth surfaces. The disclosed method entails coating affected tooth surfaces with an aqueous slurry of the present invention. Optionally, as needed, the tooth surfaces are then contacted with the slurry for a period of time until the calculus and/or plaque, so coated and contacted, has imparted thereto a visible black color. The coating and contacting steps may be carried out in essentially the same manner as the corresponding steps in the above-disclosed method for removal of calculus and plaque and stains from tooth surfaces. Optionally, as needed, the coating and contacting steps may be repeated until a sufficiently visible black color is imparted to the calculus or plaque. In a related embodiment, charcoal alone, or a charcoal and water mixture is used, essentially as described above, in a method for indicating the presence of plaque.

A related embodiment discloses a method for selectively indicating the presence of calculus, adherent to tooth surfaces. The method is carried out using the same steps as the method for indicating the presence of calculus and plaque, except that, prior to using the same steps, all tooth surfaces are first thoroughly brushed with toothpaste and flossed to remove most or substantially all of any plaque thereon.

In another aspect, the present invention is directed to a kit adapted for removing calculus, plaque or stains adherent to or otherwise attached to tooth surfaces in the oral cavity of an individual or subject. The kit provides components used in methods for such removal that are either self-practicable by an individual or practicable by an individual on a subject. The kit comprises: 1) a quantity of a disclosed aqueous slurry in a sealed container, or quantities of charcoal and a liquid portion (or constituents thereof, e.g., water and alcohol, ammonia or hydrogen peroxide) in separate sealed containers; 2) a mixing device, such as one or more stirrers, to mix the charcoal and liquid portion so as to form a slurry of the same; 3) where the charcoal and liquid portion (or constituents thereof) are provided in separate sealed containers, an additional, empty container adapted to provide a reservoir for combining measured quantities of the charcoal and liquid portion (or constituents thereof) in desired ratios; 4) one or more devices for applying the composition to affected tooth surfaces; 5) one or more devices for agitatively and frictionally (e.g., rubbing) contacting the tooth surfaces with the composition; 6) one or more devices for mechanically removing contacted calculus or plaque from the tooth surfaces; and 7) optionally, a device and/or rinsing agent for mechanically or rinsingly removing residual portions of the composition, as well as loose portions of calculus or plaque from the tooth and other surfaces of the oral cavity.

The above-mentioned devices included in the kit are as described in the previously-described methods of the present invention. In a related embodiment, disclosed is a kit wherein the devices included therein for use in the slurry application and contacting steps comprise a surface that is impregnated with charcoal.

The following example is provided for purposes of illustration, not limitation.

EXAMPLE 1

Comparison of Effectivity in Removing Calculus from Teeth Using Water, Mouthwash, a Charcoal/Mouthwash Mixture, and a Charcoal/Water Mixture Eight extracted single root, human teeth having a significant quantity of calculus adherent thereto were selected. The teeth were mounted in a block of methyl methacrylate to fit into the specimen holder of a V8 cross-brushing machine with the area of maximum calculus facing upwards out of the holding block. Each of the teeth was dried to a constant weight, the latter being accurately determined to five decimal places. They were then placed on the V8 cross-brushing machine and the tension of the toothbrushes on the affected (i.e., calculus covered) tooth surfaces was set to 150 g. All teeth specimens (specimens 1–8) were brushed for two hours: specimen 1 and 2 with deionized water, specimens 3 and 4 with Listerine® mouthwash, specimens 5 and 6 with a charcoal/water mixture; and specimens 7 and 8 with charcoal Listerine® mixture.

The charcoal was prepared by grinding aquarium grade activated carbon using a mortar and pestle until it was reduced to a fine powder. The charcoal/water mixture was prepared so as to comprise 10 g of the charcoal per 50 ml of water. The Listerine® used was the product as commercially available. The charcoal/Listerine® mixture was prepared so as to comprise 10 g of the charcoal per 50 ml of Listerine®.

After being brushed, the specimens were cleaned of loose material and again allowed to dry to a constant weight, the latter being accurately determined to five decimal places. The amount of calculus removed was, thus, determined as the difference between the pre-brushing and post-brushing weights of the specimens. The results are presented in the table below.

| Calculus Removal Agent | Tooth Specimen Weights (g) | | |
| --- | --- | --- | --- |
| | Pre-Brushing | Post-Brushing | Change |
| Water | 4.0209 ± 0.3216* | 4.0176 ± 0.3222 | 0.00335 ± 0.0006 |
| Listerine ® | 3.9882 ± 0.3937 | 3.9821 ± 0.3926 | 0.00609 ± 0.0011 |
| Charcoal/Water Mixture | 4.4103 ± 0.3339 | 4.4015 ± 0.3366 | 0.00884 ± 0.0028 |

-continued

| Calculus Removal Agent | Tooth Specimen Weights (g) | | |
|---|---|---|---|
| | Pre-Brushing | Post-Brushing | Change |
| Charcoal/ Listerine ® Mixture | 4.0083 ± 0.0712 | 3.9974 ± 0.0699 | 0.01093 ± 0.0014 |

*Mean ± SEM (N = 2)

As can be seen from the table above, brushing with water removed a very small amount of calculus. Surprisingly, brushing with the mouthwash removed a greater amount of calculus, as compared to brushing with water. The addition of the charcoal to the water thereby increased the amount of calculus removed by a factor of about 2.6, as compared to brushing with water alone. Brushing with the charcoal/Listerine® mixture resulted in the greatest amount of calculus being removed. Notably, brushing with the charcoal/Listerine® mixture yielded a calculus removal about 24% greater than that obtained by brushing with a charcoal/water mixture.

EXAMPLE 2

Measurement of Effectivity in Removing Calculus and Plaque from Canine Teeth Using a Charcoal/Mouthwash Mixture Treated was the upper left $4^{th}$ premolar tooth of a middle-aged dog, the tooth having an accumulation of dental plaque and calculus. The tooth was rated, before treatment, by a veterinarian as having a Grade III plaque accumulation and a Grade II calculus accumulation. The treatment composition used was a charcoal/mouthwash mixture comprising finely-divided charcoal and Listerine®. The mixture was applied to the tooth by dipping a cotton swab into the Listerine®, then into the finely-divided charcoal.

The tooth was rubbed with the composition for about 65 minutes using cotton-tipped swabs and wooden tooth picks. The treatment was performed without anesthetizing the dog. Roughly 50% of the rubbing was performed using the cotton swabs and 50% using the tooth picks. During the treatment, a plurality of cotton swabs were used, each swab being dipped into fresh mouthwash and charcoal, then used for rubbing the tooth with the composition for about 1–2 minutes, and then discarded. After the treatment, the plaque was completely removed (Grade 0) and the calculus accumulation was reduced to a Grade I accumulation (reduced by approximately 50% to 60%).

All of the U.S. patents, U.S. patent application publications, U.S. patent applications, foreign patents, foreign patent applications and non-patent publications listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for indicating the presence of calculus or plaque adherent to tooth surfaces, comprising the steps of:
   (a) coating the affected tooth surfaces with the aqueous slurry of divided charcoal;
   (b) optionally, contacting the affected tooth surfaces with the aqueous slurry for a period of time, such that a visible black color is imparted to the tooth surfaces thus coated and contacted;
   (c) optionally, repeating steps (a) and (b) until a sufficient quantity of the finely-divided, black charcoal has commingled with, or adhered to, the calculus or plaque so as to visibly impart thereto a black color having an intensity sufficient to indicate the presence thereof.

2. The method of claim 1 wherein step (b) comprises agitative and frictional contact of the affected tooth surfaces with the aqueous slurry.

3. A method for selectively indicating the presence of calculus, adherent to tooth surfaces, comprising the steps of:
   thoroughly brushing with toothpaste and flossing to selectively remove plaque, followed by conducting the steps of the method of claim 1.

4. A method for indicating the presence of plaque, adherent to tooth surfaces, comprising the step of:
   coating the affected tooth surfaces with finely-divided black charcoal or with a mixture of finely-divided black charcoal and water so as to impart a black color to the plaque.

* * * * *